(12) United States Patent
Patel et al.

(10) Patent No.: US 12,115,187 B1
(45) Date of Patent: Oct. 15, 2024

(54) READY-TO-USE SODIUM PHOSPHATES INJECTION

(71) Applicant: Nivagen Pharmaceuticals, Inc., Sacramento, CA (US)

(72) Inventors: Niravbhai Jayantibhai Patel, Sacramento, CA (US); Robert Miller, Sacramento, CA (US); Maheshkumar Kalubhai Bhalaria, Sacramento, CA (US); Rucha Abhijit Kelekar, Sacramento, CA (US); Brijeshkumar B Pandya, Sacramento, CA (US); Sunil Dnyanu Khandekar, Sacramento, CA (US); Sudhir Shantarum Jagdale, Sacramento, CA (US); Dasaradhi Lakkaraju, Sacramento, CA (US); Jay Shukla, Sacramento, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 0 days.

(21) Appl. No.: 18/667,826

(22) Filed: May 17, 2024

(51) Int. Cl.
*A61K 33/42* (2006.01)
*A61J 1/10* (2006.01)
*A61K 9/00* (2006.01)
*A61K 9/08* (2006.01)

(52) U.S. Cl.
CPC ............ *A61K 33/42* (2013.01); *A61J 1/10* (2013.01); *A61K 9/0019* (2013.01); *A61K 9/08* (2013.01)

(58) Field of Classification Search
None
See application file for complete search history.

(56) References Cited

U.S. PATENT DOCUMENTS 11,141,430 B1 * 10/2021 Koneru ............... A61K 9/0029

\* cited by examiner

*Primary Examiner* — Dominic Lazaro
(74) *Attorney, Agent, or Firm* — Ted Whitlock (57) ABSTRACT

Ready-to-use (RTU) Sodium Phosphates solutions for phosphorus replacement therapy are presented that include Sodium phosphate with/without sodium chloride at a fixed volume with 1.5 to 15 mmol/100 mL phosphorus, no more than 20 mEq/100 mL Sodium and less than 50 mcg/L aluminum.

15 Claims, 9 Drawing Sheets

READY-TO-USE SODIUM PHOSPHATES INJECTION

FIELD OF THE INVENTION

The field of the invention pertains to compositions and methods for preparing and using Sodium Phosphates Injection, especially as it relates to such solutions with ultra-low concentrations of aluminum, and where the solutions are packaged in a ready-to-use container at volumes and concentrations suitable for direct administration to a patient.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Hypophosphatemia is a clinical condition in which serum phosphate concentrations are less than 2.5 mg/dL (0.81 mmol/L), causing symptoms such as muscle weakness, respiratory failure, heart failure, seizures and coma. Causes of hypophosphatemia include alcohol use disorder, burns, starvation, and diuretic use. In most cases, the treatment for hypophosphatemia is phosphorus replacement therapy with an intravenous (IV) infusion at an infusion rate adjusted to the patient's age and particular need. In patients on Total Parenteral Nutrition (TPN), approximately 12 to 15 mM of phosphorus (equivalent to 372 to 465 mg elemental phosphorus) per liter bottle of TPN containing 250 g of dextrose is usually adequate to maintain normal serum phosphorus.

The suggested dose of phosphorus for infants receiving TPN is 1.5 to 2 mM P/Kg/day. Currently approved phosphorus replacement products of sodium phosphorus for IV administration may require continuous electrocardiographic (ECG) monitoring as serious cardiac reactions may occur as well as pulmonary embolisms due to pulmonary vascular precipitates. These serious cardiac and pulmonary risk factors render the accuracy of the concentration and infusion rate of the sodium phosphate critical for patient safety. Furthering these risks, the currently approved sodium phosphorus products are supplied and stored as concentrates and will therefore require aseptic compounding for the needed infusion rate, thereby increasing the risk of error and contamination. While care and monitoring may be implemented to avoid miscalculations, contamination, and serious adverse effects, preparing the IV solution by dilution and programming the correct infusion rate for administration often takes time and additional oversight. Furthermore, in most cases separate preparations are required for each of the central venous and peripheral venous administrations.

In addition, there are also potential risks with respect to chemical stability and aluminum toxicity, especially in patients with renal impairment. As is well known, phosphate solutions may be subject to crystallization and precipitation, which is exacerbated in the presence of oxygen. For that reason, concentrated solutions must be used within several hours, as any remaining volume of such solutions after limited exposure to oxygen is prone to crystallization and precipitation. However, such formulations were nevertheless concentrates and as such failed to avoid many of the difficulties associated with concentrates. With respect to levels of aluminum it should be recognized that while most currently used products are below the maximum allowed aluminum level as determined by the Federal Drug Administration (FDA), some of these aluminum concentrations may nevertheless be toxic in impaired patients. Moreover, many of the known concentrated compositions include varying amounts of sodium in the form of monobasic sodium phosphate and dibasic sodium phosphate and may not provide a proper ratio of these critical components, nor do these compositions provide a tonicity agent.

Therefore, there is still a need for Sodium Phosphates solutions with reduced aluminum content where such solutions are in a ready-to-administer formulation suitable for phosphorus replacement therapy, and where such solutions have sufficient storage stability.

These unmet needs are achieved by the composition and methods of the invention described herein. Various objects, features, aspects and advantages of the inventive subject matter are apparent from the following description and the accompanying drawings.

SUMMARY OF THE INVENTION

The inventive subject matter is directed to compositions and methods of preparation and use of a ready-to-use (RTU) Sodium Phosphates Injection for intravenous administration to patients in need thereof. Advantageously, the compositions presented herein exhibit excellent storage stability over extended periods of time, include a suitable tonicity agent, have a desirable phosphate to sodium ratio, and have an aluminum content that is equal to or less than 50 mcg/L. Such solutions do not require dilution or other manipulation prior to use and can be administered as a single unit at a rate of administration that does not require specific calculations.

One aspect of the inventive subject matter comprises an isotonic or hyper-isotonic sterile ready-to-use (RTU) aqueous Sodium Phosphates Injection solution that comprises sodium phosphates, wherein the solution includes 15 mmol/100 mL phosphorus (0.15 mmol/mL) and equal or less than 25 mcg/L aluminum.

In an embodiment of the invention, the sodium phosphates comprise monobasic sodium phosphate ($NaH_2PO_4$) and dibasic sodium phosphate ($Na_2HPO_4$), wherein the monobasic sodium phosphate (monohydrate) is present in the solution an amount of about 1380 mg/100 mL and dibasic sodium phosphate is present in the solution in an amount of about 710 mg/100 mL. Preferably, the solution has a pH of between 6.2 and 6.8. Similarly, two different concentrations wherein the monobasic sodium phosphate (monohydrate) is present in the solution an amount of 1380 mg/250 mL (i.e., 15 mmol/250 mL), 1.38 mg/mL (i.e., 1.5 mmol/100 mL), and dibasic sodium phosphate is present in the solution in an amount of about 710 mg/250 mL (i.e., 15 mmol/250 mL), 0.71 mg/mL (i.e., 1.5 mmol/100 mL) and sodium chloride is present in the two diluted concentrations in 5.5 mg/mL and 9 mg/mL, respectively, wherein the sodium chloride-containing solution has a pH range of 6.0-8.0.

In a preferred embodiment, the solution is packaged in a flexible (e.g., polyolefin) container, typically at a volume of 100 mL or 250 mL, providing a sterile, ready-to-use (RTU)

premixed pharmaceutical product. The flexible polyolefin container may optionally be contained in a secondary metallized overwrap.

In one embodiment, the pharmaceutical product of the invention can comprise Sodium Phosphates Injection solution, wherein the solution includes less than 25 mcg/L aluminum. Phosphorus concentrations can be provided having (a) about 15 mmol/100 mL phosphorus, (b) about 15 mmol/250 mL phosphorus, or (c) about 1.5 mmol/100 mL phosphorus. In some embodiments, the premixed pharmaceutical product will comprise about 4.65 mg/mL of phosphorus in a 100 mL premixed container, or about 1.86 mg/mL of phosphorus for a 250 mL premixed container In use, a method of administering phosphates to a patient in need of phosphorus replacement therapy, in accordance with the subject invention, comprises a step of administering to the patient, without prior dilution, an isotonic or hyper-isotonic, sterile, and ready-to-use (RTU) solution comprising sodium phosphates and sodium chloride from a flexible container at a rate of infusion and by a route of administration corresponding to the patient's age and degree of need of phosphorus replacement. Preferably, the administered RTU solution comprises about 15 mmol/100 mL or 15 mmol/250 mL phosphorus, and less than 25 mcg/L aluminum. Advantageously, a RTU solution of the invention can be administered after extended storage (e.g., storage for at least 3 months at 25° C. and 40% relative humidity).

DETAILED DESCRIPTION

The inventors have now discovered and prepared Sodium Phosphates solutions that are storage stable, sterile, and ready-to-use (RTU), and as such avoid all of the drawbacks of heretofore known concentrated Sodium Phosphates solutions that required prior dilution or manipulation and had no significant shelf life. Moreover, the Sodium Phosphates solutions presented herein have a desirably low aluminum concentration and provide phosphates and sodium at ratios that are suitable for facile administration. Further, the solutions according to the invention are preservative-free and have osmolality and pH suitable for direct administration.

For example, a 100 mL of the RTU solution of the invention, comprising sodium chloride, about 15 mmol total phosphates, and aluminum at a concentration equal to or less than 25 micrograms/liter (mcg/L or μg/L) packaged into a flexible polymeric container allows for simple and direct administration to a patient without the need for prior dilution or other manipulation, and can be infused via a pump at a single infusion rate to deliver appropriate quantities of phosphates and sodium. Moreover, and as described in more detail herein, the solutions of the invention exhibit excellent storage stability, remaining fee of crystallization or precipitation of the phosphates or other salts, and remain free of microbial growth for up to 12 months. Compositions of the invention comprising the specified quantities of phosphates and sodium advantageously enable administration to an adult or pediatric patient via peripheral venous administration or central venous administration.

One preferred premixed pharmaceutical product in accordance with the invention, comprising (in injectable water) 13.8 mg/mL $NaH_2PO_4$ and 7.1 mg/mL $Na_2HPO_4$ for a total 0.15 mmol/mL of phosphates, provides a desirable phosphates-to-sodium ratio. Notably, such solutions provide a pH between 6.0 and 7.0. which is suitable for injection, and tonicity that is desirable and suitable for direct intravenous injection.

The terms "ready-to-use" or "RTU" are interchangeable and refer to a solution that can be directly administered to a patient without prior dilution or other adjustment such as addition of saline or other tonicity agent. A "ready-to-use" or "RTU" solution can be delivered from a storage container via peripheral or central catheter to a patient without additional manipulation of the solution in the storage container. The terms "ready-to-use" and "RTU" are also interchangeably used with the term "ready-to-administer."

As used herein, the term "phosphorus" is used interchangeably with the term "phosphate" or "phosphates" and refers to the $PO_4^{3-}$ anion, regardless of its protonation state and/or presence of counterion(s). Thus, the term phosphorus can refer to $Na_2HPO_4$, $NaH_2PO_4$, $HPO_4^{2-}$, $H_2PO_4^-$, and/or $PO_4^{3-}$.

The term "aluminum" as used herein refers to both aluminum ions (e.g., $Al^{3+}$) as well as metallic aluminum.

The term "sodium" as used herein refers to the cationic forms of sodium ($Na^+$).

A RTU Sodium Phosphates Injection solution of the invention comprises aluminum at a concentration of less than 100 mcg/L, less than 90 mcg/L, less than 80 mcg/L, less than 70 mcg/L, less than 60 mcg/L, less than 55 mcg/L, less than 50 mcg/L, less than 45 mcg/L, less than 40 mcg/L, less than 35 mcg/L, or less than 30 mcg/L. Preferably, a composition of the invention comprises a concentration of aluminum equal to or less than 25 micrograms/liter (mcg/L or μg/L). A composition of the invention is advantageously more efficient, effective, and safe (e.g., less risk of contamination) to prepare and administer More preferably, the Sodium Phosphates solution has an aluminum content of no more than 50 mcg/L, not more than 49 mcg/L, not more than 48 mcg/L, not more than 47 mcg/L, not more than 46 mcg/L, 45 mcg/L, 44 mcg/L, 43 mcg/L, 42 mcg/L, 41 mcg/L, 40 mcg/L, 39 mcg/L, 38 mcg/L, 37 mcg/L, 36 mcg/L, 35 mcg/L, 34 mcg/L, 33 mcg/L, 32 mcg/L, 31 mcg/L, 30 mcg/L, 29 mcg/L, 28 mcg/L, 27 mcg/L, 26 mcg/L, 25 mcg/L, 24 mcg/L, 23 mcg/L, 22 mcg/L, 21 mcg/L, 20 mcg/L, 15 mcg/L, 10 mcg/L, or not more than 8 mcg/L.

In exemplary embodiments, the RTU Sodium Phosphates Injection solution of the invention includes monobasic sodium phosphate ($NaH_2PO_4$) and dibasic sodium phosphate ($Na_2HPO_4$). Typically, the monobasic sodium phosphate (monohydrate) is at an amount of about 1380 mg/100 mL and the dibasic sodium phosphate is at an amount of about 710 mg/100 mL. Alternatively, an embodiment of a sterile RTU aqueous Sodium Phosphates Injection solution of the invention comprises 15 mmol/250 mL total phosphates. Yet another embodiment of the invention comprises 1.5 mmol/100 mL total phosphates. Sodium chloride can be included at an amount of about 5.5 mg/mL for 250 mL and about 9 mg/mL for 100 mL container.

In preparing a composition of the invention, the method of making aqueous Sodium Phosphates Injection solutions include an initial step of adding salt components to water (preferably, water-for-injection, or "WFI"). These salt components are preferably selected based on aluminum content. Sodium hydrogen phosphate comprising 5 ppm (ppm, approximately 0.7 mmol/100 mL) or less of aluminum, sodium dihydrogen phosphate comprising 5 ppm or less of aluminum, and, when present, sodium chloride comprising 5 ppm or less of aluminum, are preferred. More preferably, each of these components comprise not more than 4 ppm, not more than 3 ppm, not more than 2 part per million, or not more than 1 ppm of aluminum. Accordingly, and in contrast to the currently available products, aluminum content is reduced based on the aluminum content in the starting materials, at the initial dissolution step of preparation, thereby avoiding unwanted or excessive aluminum levels, as described, in the solutions presented herein.

It is preferred that the solutions presented herein are stored in an autoclavable flexible polymeric container. Notably, certain polymeric materials can affect chemical and storage stability. For example, some polymeric materials were prone to produce higher quantities of crystallized material and/or precipitates (e.g., at an average particle size of about 10 micron or 25 micron), whereas certain other materials were unexpectedly prone to water loss due to water vapor permeability, particularly at extended periods of storage (e.g., one to several months). Therefore, a secondary cover or overwrap of the polymeric material is preferred in order to maintain predetermined concentration of all solutes. Among other materials as are known in the art, particularly preferred overwrap materials comprise polymeric composite films with at least one metal (e.g., aluminum) layer.

With respect to suitable polymeric autoclavable materials, preferred polymeric materials include polysulfone, polycarbonate, polypropylene, polyethylene (LDPE or HDPE), ethylene/propylene copolymers, polyolefins, acrylic-imide copolymers, polyester (e.g., PET, PEN and the like), TEFLON®, NYLON®, acetal (DELRIN®), polymethylpentene, PVDC, ethylvinylacetate, polyvinyl chloride, and polyolefins. Polyolefin containers are preferred because they remain transparent and dimensionally stable, even after autoclaving.

As will be readily appreciated, the polymeric containers can be prepared in numerous form factors, however, flexible bags are especially preferred. Likewise, the volume of the polymeric container may change considerably. However, it is typically preferred that the container has a volume that accommodates the volume of solution required for a single and complete administration of the solutions presented herein. Therefore, a particularly preferred internal volume of the container is 100 mL. Moreover, it should be appreciated that the polymeric container will have a single or a double port that is typically sealed with a stopper as is well known in the art.

The Sodium Phosphates Injection solution of the invention, packaged in a flexible polymeric container, can be sterilized in the container by steam sterilization (e.g., autoclaving, 121° C., for about 15 minutes). Suitable containers can undergo autoclaving without altering the thermal properties of the film layers, ports, and closure system, and maintain the integrity of the flexible container. In more typical embodiments, the premixed or ready-to-use stable pharmaceutical, formulation of Sodium Phosphates Injection at 15 mmol/100 mL of phosphorus or 15 mmol/250 mL of phosphorus is packaged in a non-PVC plastic container with ports and container closure systems, which is terminally sterilized at a temperature of at least about 110° C. to 130° C. via autoclaving with a dwelling time ranging from 7 to 30 minutes.

An exemplary process of making a RTU phosphates solution of the invention includes the steps of:

adding Dibasic Sodium Phosphate to water at a concentration of 1380 mg/100 mL with stirring, wherein the Dibasic Sodium Phosphate contains no more than 2 ppm aluminum, adding Monobasic Sodium Phosphate to the water at a concentration of 710 mg/100 mL with stirring, wherein the Monobasic Sodium Phosphate contains no more than 2 ppm aluminum, and thereby forming the aqueous Sodium Phosphates solution, and optionally adding sodium chloride in concentrations of 5.5 mg/mL and 9.0 mg/mL.

Addition of sodium chloride is preferred in a solution of the invention comprising 15 mmol/250 mL and 1.5 mmol/100 mL.

In additional or alternative embodiments, the method of making the aqueous Sodium Phosphates Injection solution includes filter sterilizing a fixed volume of the aqueous Sodium Phosphates Injection solution into a flexible container. The flexible container and solution can be terminally sterilized. Preferably, the terminal sterilization is autoclaving to sterility. For storage and/or transport of the terminally sterilized flexible container of RTU aqueous Sodium Phosphates Injection solution, the flexible container may be placed inside an aluminum pouch for protective storage and transport.

In contrast to current practice where remaining concentrated phosphates solutions after withdrawal must be discarded after 24-48 hours (due to crystallization and/or precipitation issues), the inventors unexpectedly discovered that the RTU solutions could remain chemically stable and did not undergo microbial spoilage. Stability and/or concentration of the cations and anions was further promoted where the autoclaved container was packaged into a secondary container, such as a metal foil overwrap and/or where the space between the polymeric container and overwrap is flushed with nitrogen or other inert gas to remove oxygen before sealing the secondary (overwrap) container. The inventors also observed that the type of polymer had at least some influence on storage stability and dimensional stability under autoclaving conditions.

Based on stability studies performed by the inventors, a solution of the subject invention can be stored more than the 48-hour limitation of current formulations, and is stable for extended periods. For example, a solution of the subject invention can be stable for at least 1 month, at least 3 months, at least 6 months, at least 1 year, or even longer without significant changes in the product composition. Such storage can be performed at ambient conditions (e.g., 25° C., 40% relative humidity), without refrigeration, at warm conditions (e.g., 30° C., 65% relative humidity), and even at accelerated storage conditions (e.g., 40° C., 15% relative humidity).

Notably, the inventive RTU aqueous Sodium Phosphates Injection solution is efficiently administered to a patient in need of phosphorus replacement therapy. Advantageously, the method includes easily administering to the patient a sterile ready-to-use (RTU) Sodium Phosphates Injection solution taken directly from the flexible container. A solution of the subject invention can be administered by intravenous injection or infusion at a rate of infusion and by a route of administration corresponding to the patient's age and degree of need of phosphorus replacement. As the flexible container comprises a fixed volume (e.g., 100 mL) of the sterile RTU Sodium Phosphates Injection solution includes 15 mmol/100 mL Phosphorus, administration to an adult or pediatric patient by peripheral venous catheter or central venous catheter may be readily accomplished based on programming the infusion rate accordingly.

In patients on Total Parenteral Nutrition (TPN) therapy, approximately 12 to 15 mM of phosphorus (equivalent to 372 to 465 mg elemental phosphorus) per liter bottle of TPN solution containing 250 g dextrose can be administered to maintain normal serum phosphorus, though larger amounts may be required in hypermetabolic states. The amount of sodium and phosphorus, which accompanies the addition of sodium phosphate also should be kept in mind, and if necessary, serum sodium levels should be monitored.

The suggested dose of phosphorus for infants receiving TPN is 1.5 to 2 mmol phosphorus/kg/Day. Parenteral drug products should be inspected visually for particulate matter and discoloration prior to administration, whenever solution and container permit.

Examples

A. Formulation of Ingredients for Sodium Phosphates in Sodium Chloride Injection.

For a 15 mmol/100 mL concentration of phosphorus, as shown in Table 1, 13.8 mg/mL $NaH_2PO_4$ and 7.1 mg/mL $Na_2HPO_4$ are added to water with mixing as disclosed herein. Add tonicity agent (if applicable) into the solution and dissolve until a clear solution is obtained. Check the pH of solution. Make up the volume to 100% by adding water. The Water for Injection is to volume (quantum satis, abbreviated as q.s.), which for the ready-to-use (RTU) formulation disclosed herein, is fixed at 100 mL. Filter the solution using 0.22-micron Filter and fill into in IV flexible container.

TABLE 1

Formulation composition of Sodium Phosphates Injection

| Ingredients Details | Function | Formulation Compositions (mg/mL) | | | | |
| --- | --- | --- | --- | --- | --- | --- |
| | | A (15 mmol P/100 mL) | B (15 mmol P/250 mL) | C (15 mmol P/100 mL) | D (15 mmol P/250 mL) | E (1.5 mmol P/100 mL) |
| Sodium Phosphate monobasic, monohydrate | Active | 13.8 mg | 5.52 mg | 13.8 mg | 5.52 mg | 1.38 mg |
| Sodium Phosphate dibasic | | 7.1 mg | 2.84 mg | 7.1 mg | 2.84 mg | 0.71 mg |
| Sodium Chloride | Tonicity Agent | — | 5.5 mg | — | — | 9.0 mg |
| Dextrose Monohydrate | | — | — | 50 mg | 50 mg | — |
| Water for Injection | Vehicle | q.s. to 1 mL | | | | |

Bulk or batch solution for aliquoting can also be prepared, following the process described above, and concentrations and volumes of ingredients as presented in Table 2, below.

TABLE 2

Batch formulation of Sodium Phosphates injection solution (15 mmol P/100 mL).
Formulation for Bulk solution of Sodium Phosphates in Sodium Chloride Injection, RTU

| | Batch Size: 1000 mL | |
| --- | --- | --- |
| Active and Excipient Details | Composition per mL | Batch qty. per 1000 mL |
| Sodium Phosphate monobasic | 13.8 mg | 13.8 g or 13800 mg |
| Sodium Phosphate dibasic | 7.1 mg | 7.1 g or 7100 mg |
| Water for Injection | 1 mL | 1000 mL |

Properties and specifications for an acceptable solution of the invention are shown in Table 3, below.

TABLE 3

Specification of Sodium Phosphates Injection, RTU

| No. | Test | Release Specification | Shelf-Life Specification | Reference |
|---|---|---|---|---|
| 1. | Description | Clear, colorless solution, free from visible particles. | Clear, colorless solution, free from visible particles. | In-House |
| 2 | Identification Tests | | | |
| | Sodium | Meet the requirement | Meet the requirement | USP <191> |
| | Phosphate | Meet the requirement | Meet the requirement | |
| | Chloride | Meet the requirement | Meet the requirement | |
| 3. | pH | 6.0 to 8.0 | 6.0 to 8.0 | USP <791> |
| 4. | Osmolality | 250-350 mOsmol/kg | 250-350 mOsmol/kg | USP <785> |
| 5. | Assay of Sodium (Label Claim: Each mL contains 4.60 mg of Sodium) | Not less than 90.0% and Not more than 110.0% | Not less than 90.0% and Not more than 110.0% | In-house |
| 6. | Assay of Phosphorus (Label Claim: Each mL contains 4.65 mg of Phosphorus) | Not less than 90.0% and Not more than 110.0% | Not less than 90.0% and Not more than 110.0% | In-house |
| 7. | Particulate matter A) Visible particles | | | USP<790> |
| | Visual inspection | Should be free of visible particles | Should be free of visible particles | |
| | Particulate matter B) Sub-visible Particles (By Light Obscuration method) | | | USP<788> Method-I |
| | ≥10 µm size particles | As per USP | As per USP | |
| | ≥25 µm size particles | As per USP | As per USP | |
| 8 | Container content for Injections | Not less than the nominal volume | Not less than the nominal volume | USP<697> |
| 9. | Sterility | Meets the requirement | Meets the requirement | USP<71> |
| 10 | Bacterial endotoxins | Not more than 1.10 USP EU/mg of sodium phosphates | Not more than 1.10 USP EU/mg of sodium phosphates | USP<85> |
| 11 | Residual Solvents | Meets the requirement | Not Applicable | USP <467> |
| 12 | Container Closure integrity test | Meets the requirement | Meets the requirement | USP <1207.2> |
| 13 | Weight loss | Not Applicable | NMT 5% | In-House |
| 14 | Elemental Impurities | Meets the requirement of USP <232/233> and ICH Q3D (Option 3 Finished product analysis) | Not Applicable | USP <232/233>/ICH Q3D |
| 15 | Aluminum content | Not more than 25 µg/L | Not more than 25 µg/L | In-house |
| 16 | Compliance with USP <1> | Complies | Not Applicable | USP <1> |

B. Ion Chromatography Methods:

Assay of Anions (Phosphorus and Chloride) and Cations (Sodium) By Ion Chromatography: All the solution preparations (Mobile Phase, Standard, Sample) should be prepared in plastic ware (Volumetric flask, beakers, pipette tips, eluent bottles, etc.).

Preparation of Mobile Phases:

Mobile Phase for Anions (9 mM Na2CO3): Take 18.0 mL of Dionex Sodium Carbonate concentrate (0.5M) and dilute to 1000 mL with IC grade water (18.2 MΩ·cm, 0.22 µm filtered), mixed well and degas it for 10 minutes. Purge the solution with helium at 8-10 psi for 10 minutes. After purging blanket/pressurize the container with helium at 8-10 psi for 10 minutes.

Mobile Phase for Cations (20 mm Methanesulfonic Acid (MSA)): Take 50.0 mL of Dionex CS12A Eluent concentrate (0.4M Methanesulfonic Acid) and dilute to 1000 mL with IC grade water (18.2 MΩ·cm, 0.22 µm filtered), mixed well and degas it for 10 minutes.

Diluent: Use IC grade water (18.2 MΩ·cm, 0.22 µm filtered) as Diluent.

IC Conditions: The liquid chromatography equipped with conductivity detector, an injector and a data processor. Chromatographic Conditions for Anions are shown below in Table 4.

TABLE 4

Chromatographic Conditions for Anions

| Parameters | Conditions |
|---|---|
| Guard Column | Dionex IonPac RFIC AG9-HC (2 × 50 mm) |
| Column | Dionex IonPac RFIC AS9-HC (2 × 250 mm) |
| Flow rate | 0.4 mL/min. |
| Detector | Suppressed conductivity |
| Injection volume | 50 µL |
| Run time | 15 Minutes |
| Cell Temperature | 30° C. |
| Sample Cooler Temp. | 25° C. |
| Suppressor | AERS 500e 2 mm (constant voltage & recycle mode) (18 mA) |

Chromatographic Conditions for Anions for a different sized column, higher flow rates, and different Suppressor, are shown in Table 5.

TABLE 5

Chromatographic Conditions for Anions

| Parameters | Conditions |
|---|---|
| Guard Column | Dionex IonPac RFIC CG12A (4 × 50 mm) |
| Column | Dionex IonPac RFIC CS12A (4 × 250 mm) |

TABLE 5-continued

Chromatographic Conditions for Anions

| Parameters | Conditions |
| --- | --- |
| Flow rate | 0.7 mL/min. |
| Detector | Suppressed conductivity |
| Injection volume | 50 μL |
| Run time | 15 Minutes |
| Cell Temperature | 30° C. |
| Sample Cooler Temp. | 25° C. |
| Suppressor | CDRS 600 4 mm (constant voltage & recycle mode) (41 mA) |

C. Preparation of Analytical Solutions:

Preparation of Standard Solution-1 Set-1 (for Anions):

Transfer 0.93 mL of Phosphate Phosphorus Standard Solution for IC into 50 mL of plastic volumetric flask made up to the mark with diluent, mixed well. Further diluted 5.0 mL above solution into 25 mL of plastic volumetric flask made up to the mark with diluent, mixed well. (This solution contains 3.720 μg/mL of Phosphorus).

Preparation of Standard Solution-1 Set-2 (for Anions):

Transfer 0.93 mL of Phosphate Phosphorus Standard Solution for IC into 50 mL of plastic volumetric flask made up to the mark with diluent, mixed well. Further diluted 5.0 mL above solution into 25 mL of plastic volumetric flask made up to the mark with diluent, mixed well. (This solution contains 3.720 μg/mL of Phosphorus).

Preparation of Standard Solution-2 Set-1 (for Cations):

Transfer 0.92 mL of Sodium Standard Solution for IC into 50 mL of plastic volumetric flask made up to the mark with diluent, mixed well. Further diluted 5.0 mL above solution into 25 mL of plastic volumetric flask made up to the mark with diluent, mixed well. (This solution contains 3.680 μg/mL of Sodium).

Preparation of Standard Solution-2 Set-2 (for Cations):

Transfer 0.92 mL of Sodium Standard Solution for IC into 50 mL of plastic volumetric flask made up to the mark with diluent, mixed well. Further diluted 5.0 mL above solution into 25 mL of plastic volumetric flask made up to the mark with diluent, mixed well. (This solution contains 3.680 μg/mL of Sodium).

Preparation of Sample Solution:

Transfer the required amount of Finished Product into 100 mL of plastic volumetric flask made up to the mark with diluent, mixed well. Further diluted 4.0 mL above solution into 50 mL of plastic volumetric flask made up to the mark with diluent, mixed well. (This solution contains 3.720 μg/mL of Phosphorus). Calculations % Assay is calculated as follows:

$$\frac{Ru}{Rs} \times \frac{Vs}{25} \times \frac{5.0}{25} \times \frac{100}{Vt} \times \frac{50}{4.0} \times \frac{P}{L.C.}$$

where Ru is Average Peak area of each individual peak in Sample Solution, Rs is Average Peak area of each individual peak in Standard Solution Set-1, Vs is Volume of each Anion Standards (Phosphorus and Chloride) and Cation Standards (Sodium and Sodium) (in mL), Vt is Volume of Sample Solution (in mL), P is Potency of each individual Standard, and L.C. is Label Claim of each Anions and Cations as follows: Phosphorus (Anion)—4.65 mg/mL and Sodium (Cation)—4.60 mg/mL.

D. Stability Studies

For the stability studies, the inventors investigated stability of a Sodium Phosphates Injection containing saline that was prepared using monobasic sodium phosphate ($NaH_2PO_4$) and dibasic sodium phosphate ($Na_2HPO_4$), wherein the monobasic sodium phosphate was present in the solution in an amount of about 1380 mg/100 mL and the dibasic sodium phosphate was present in the solution in an amount of about 710 mg/100 mL (Formulation A). Thus, the Formulation A solution contained 15 mmol/100 mL phosphorus (0.15 mmol/mL) and had an aluminum content of about less than 25 mcg/L. A summary of the properties of this formulation is shown in Table 6, below.

TABLE 6

Properties of Formulation A
Sodium Phosphates Injection (15 mmol of Phosphorus/100 mL)
Formulation A (TS @ 121° C. for 15 minutes)

| | Condition | | | | |
| --- | --- | --- | --- | --- | --- |
| Test | Initial | 1M 25/40 | 1M 40/15 | 3M 25/40 | 3M 40/15 |
| Description* | CCS | CCS | CCS | CCS | CCS |
| pH of Solution | 6.52 | 6.47 | 6.48 | 6.49 | 6.48 |
| Osmolality (mOsm/kg) | 290 | 307 | 305 | 283 | 287 |
| LPC   10 μm | 148 | 197 | 687 | 53 | 327 |
|          25 μm | 12 | 10 | 103 | 7 | 27 |
| Assay of        % Anions   Phosphorus | 100.3% | 98.3% | 97.9% | 100.8% | 98.8% |
| Assay of        % Cations    Sodium | 98.9% | 97.0% | 98.4% | 98.8% | 97.7% |
| Aluminum Content | 4 | 5 | 5 | 6 | 5 |

*CCS-A Clear colorless solution, free from visible foreign particles

Stability was also investigated for a Sodium Phosphates Injection containing saline (sodium chloride solution). Formulation B was prepared using monobasic sodium phosphate ($NaH_2PO_4$), dibasic sodium phosphate ($Na_2HPO_4$), wherein the monobasic sodium phosphate was present in the solution in an amount of about 1380 mg/250 mL, the Dibasic Sodium Phosphate was present in the solution in an amount of about 710 mg/250 mL, and sodium chloride was present at a concentration of 5.5 mg/mL. Thus, the Formulation B solution contained 15 mmol/250 mL phosphorus (0.06 mmol/mL) and had an aluminum content of about less than 25 mcg/L. A summary of the properties of this formulation is shown in Table 7, below.

TABLE 7

Properties of Formulation B
Sodium Phosphates Injection
(15 mmol of Phosphorus/250 mL) (5.5 mg/mL of Sodium Chloride)
Formulation B (TS @ 121° C. for 15 minutes)

| | Condition | | | | |
| --- | --- | --- | --- | --- | --- |
| Test | Initial | 1M 25/40 | 1M 40/15 | 3M 25/40 | 3M 40/15 |
| Description* | CCS | CCS | CCS | CCS | CCS |
| pH of Solution | 6.49 | 6.44 | 6.44 | 6.43 | 6.43 |
| Osmolality (mOsm/kg) | 294 | 308 | 309 | 287 | 286 |
| LPC   10 μm | 6.73 | 3.80 | 6.53 | 0.87 | 1.73 |
|          25 μm | 0.20 | 0.40 | 0.53 | 0.20 | 0.13 |
| Assay of        % Anions   Phosphorus | 100.4% | 101.9% | 99.2% | 99.7% | 99.7% |
|          % Chloride | 98.2% | 98.5% | 95.7% | 96.4% | 96.5% |

TABLE 7-continued

Properties of Formulation B
Sodium Phosphates Injection
(15 mmol of Phosphorus/250 mL) (5.5 mg/mL of Sodium Chloride)
Formulation B (TS @ 121° C. for 15 minutes)

| | | Condition | | | |
|---|---|---|---|---|---|
| Test | Initial | 1M 25/40 | 1M 40/15 | 3M 25/40 | 3M 40/15 |
| Assay of Cations % Sodium | 96.7% | 100.7% | 98.0% | 96.6% | 96.5% |
| Aluminum Content | 3 | 2 | 2 | 4 | 6 |

*CCS-A Clear colorless solution, free from visible foreign particles

Figure 1A:
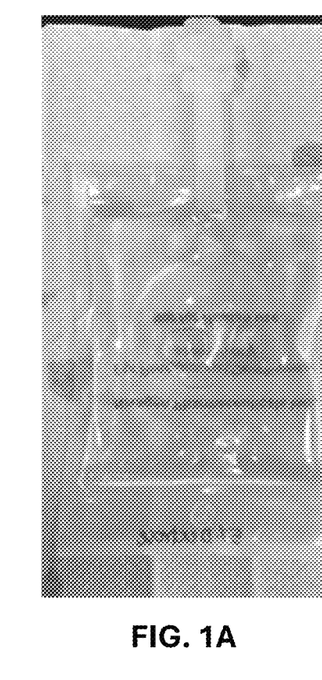
FIG. 1A is a photograph showing a packaged Formula C composition before terminal sterilization.
Figure 1B:
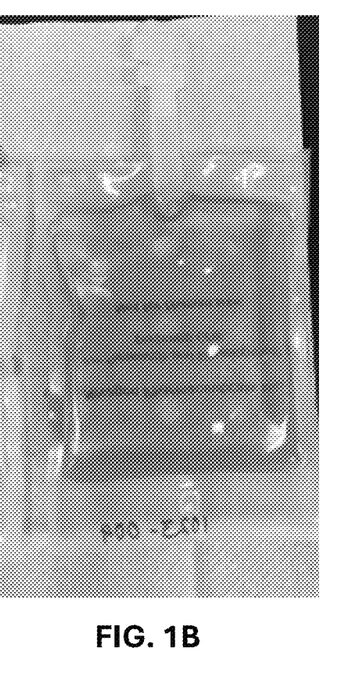
FIG. 1B is a photograph showing a packaged Formula C composition after terminal sterilization, illustrating discoloration of the contained solution.

Formulation C was prepared the same as Formulation A, above, but in dextrose-containing solution. Upon being terminally sterilized at 121° C. for 15 minutes, Formulation C charred and the solution turned brown-to-dark brown in color. FIG. 1A shows Formulation C before terminal sterilization (at 121° C. for 15 minutes), illustrating a clear, colorless solution (CSS). FIG. 1B shows Formulation C after terminal sterilization, showing its brownish discoloration, likely due to caramelization of the sugar.

Figure 1C:
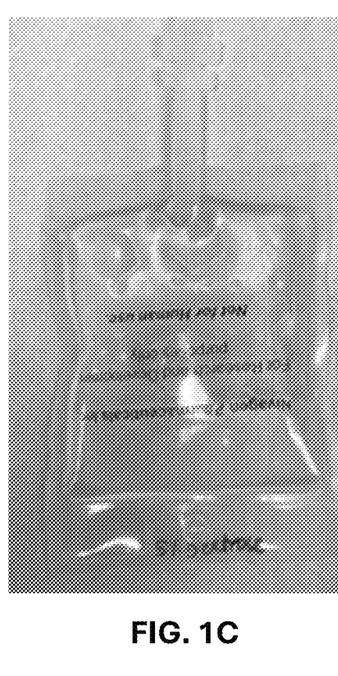
FIG. 1C is a photograph showing a packaged Formula D composition before terminal sterilization.
Figure 1D:
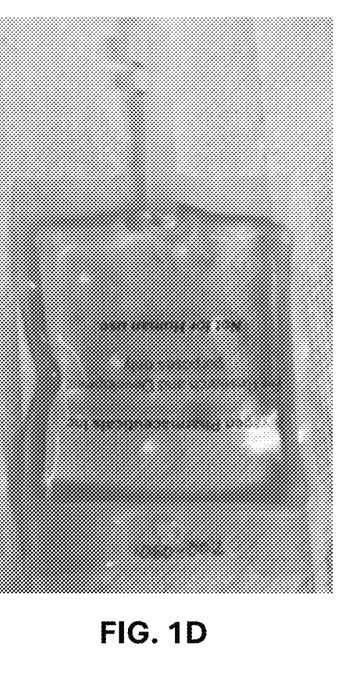
FIG. 1D is a photograph showing a packaged Formula D composition after terminal sterilization, illustrating discoloration of the contained solution.
Figure 2:
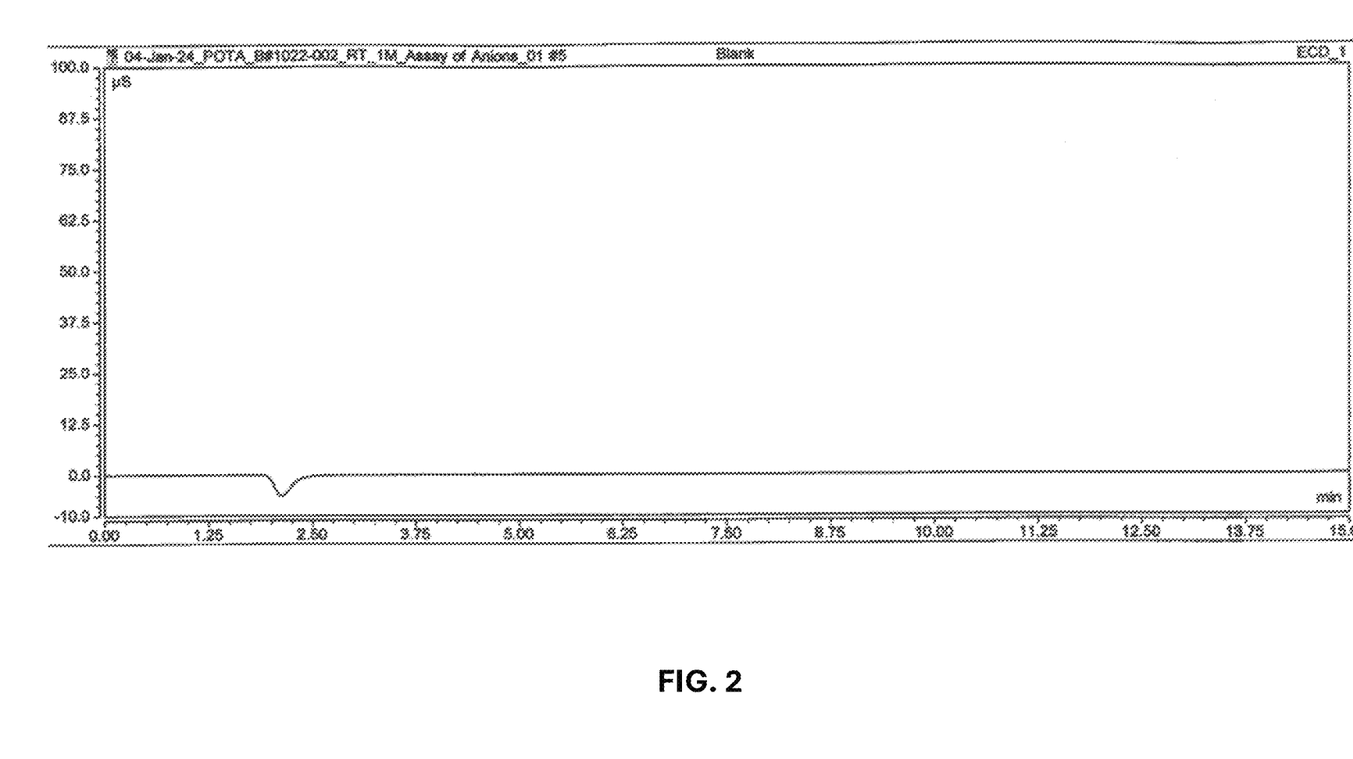
FIG. 2 is a chromatogram of a blank solution (for Anion).
Figure 3:
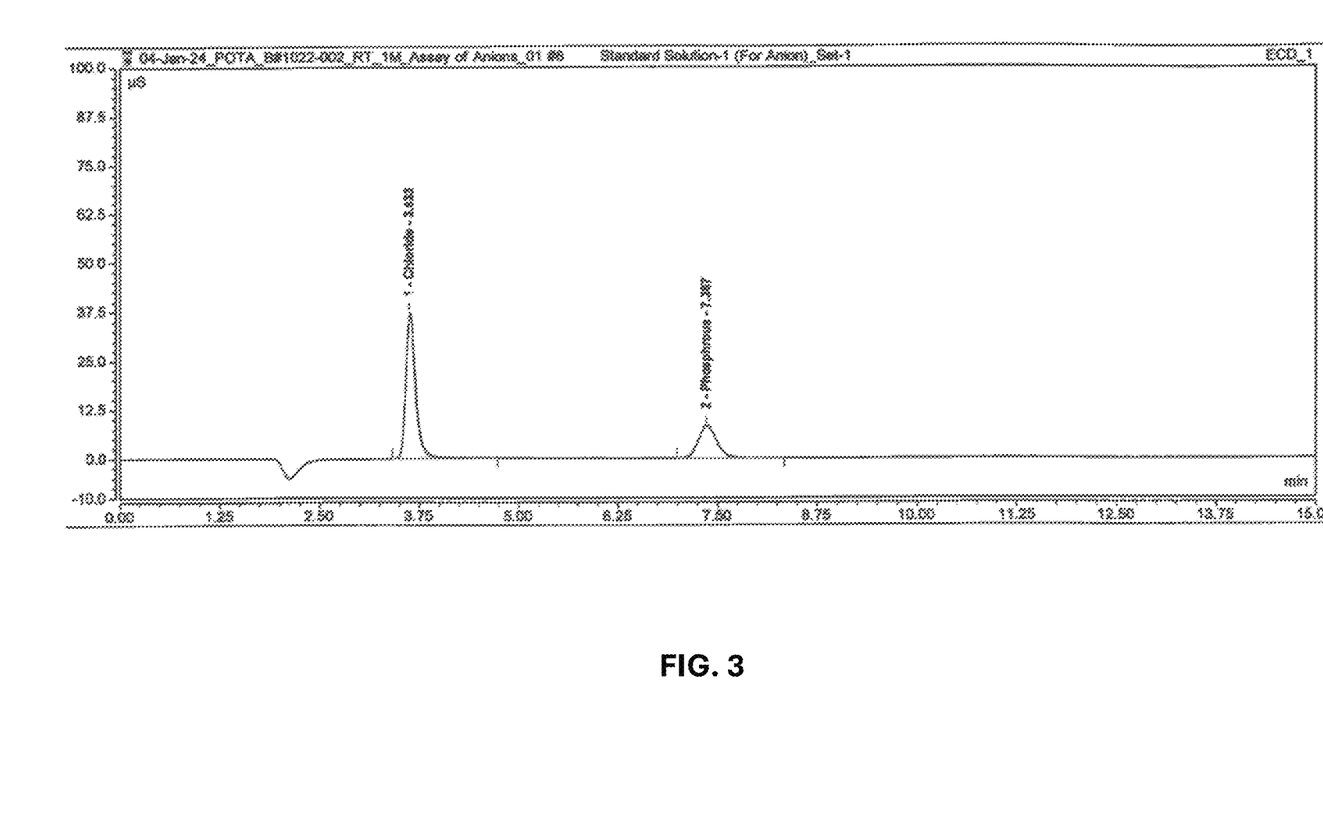
FIG. 3 is a chromatogram of the Standard solution (for Anion).
Figure 4:
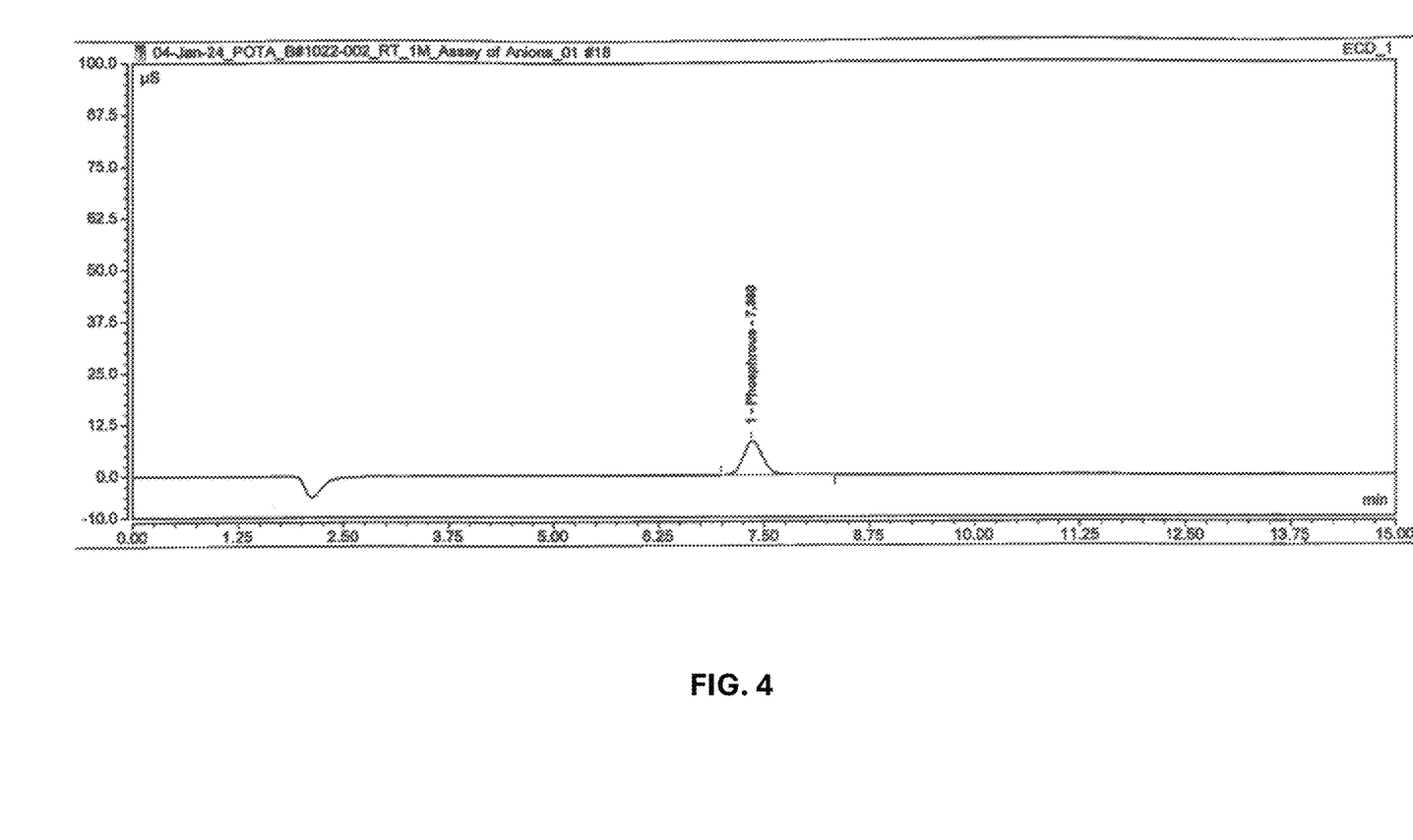
FIG. 4 is a chromatogram of a Test sample, 15 mmol P/100 mL (for Anion).
Figure 5:
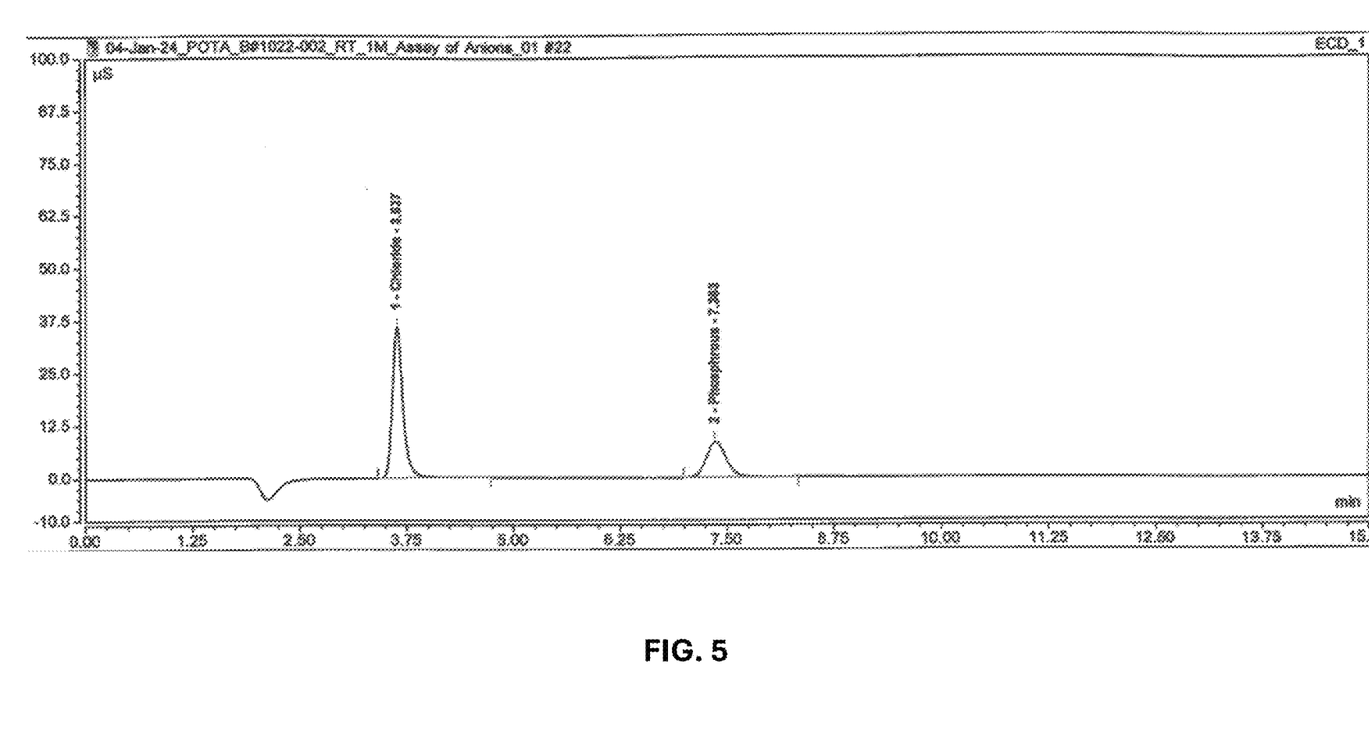
FIG. 5 is a chromatogram of a Test sample, 15 mmol P/250 mL (for Anion).
Figure 6:
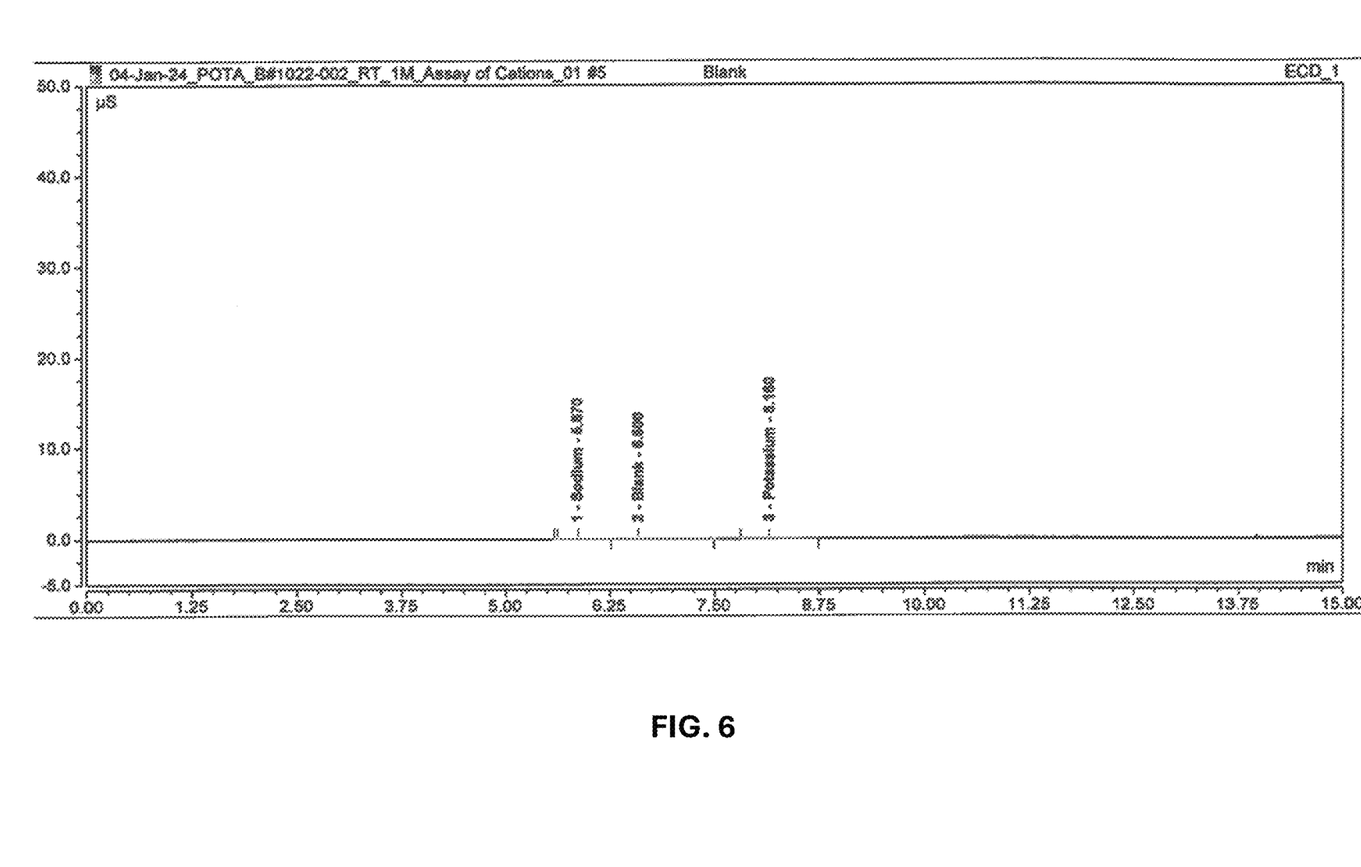
FIG. 6 is a chromatogram of a blank solution (for Cation).
Figure 7:
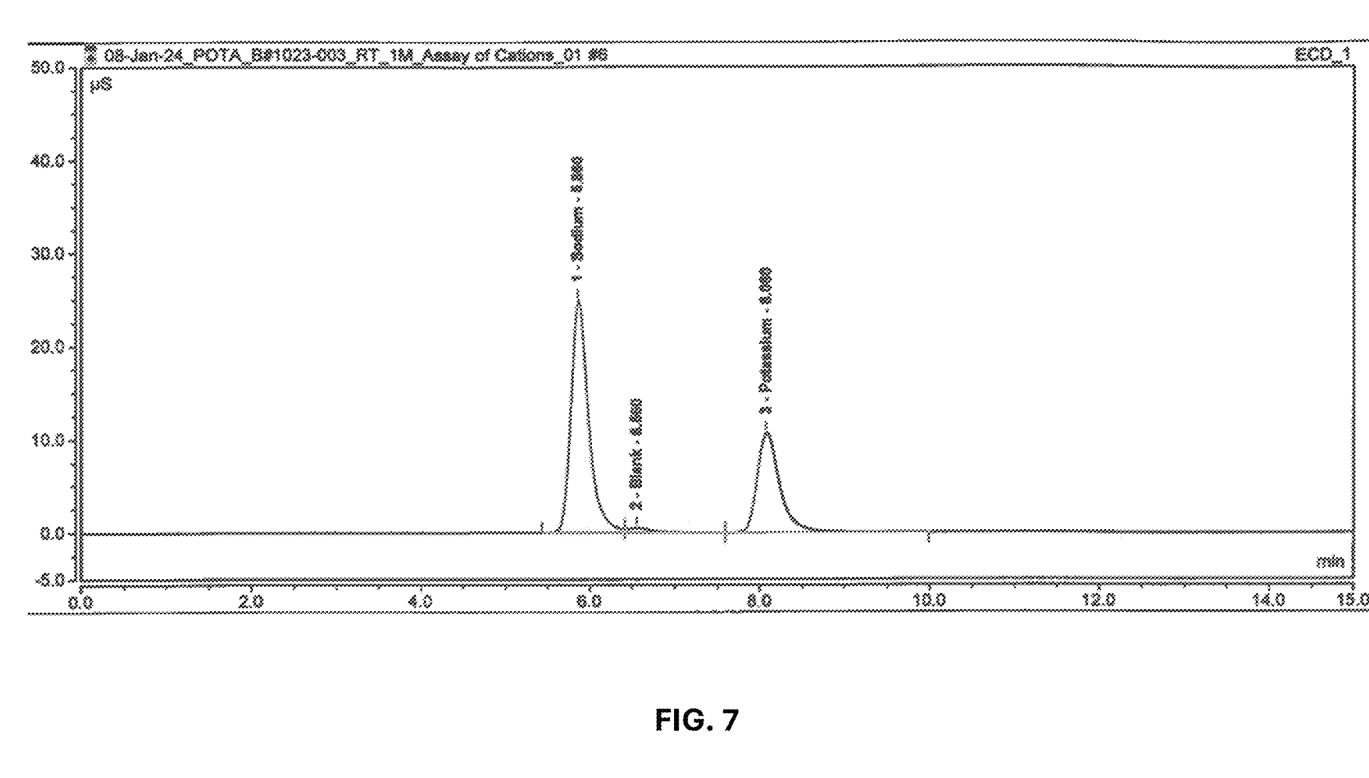
FIG. 7 is a chromatogram of the Standard solution (for Cation).
Figure 8:
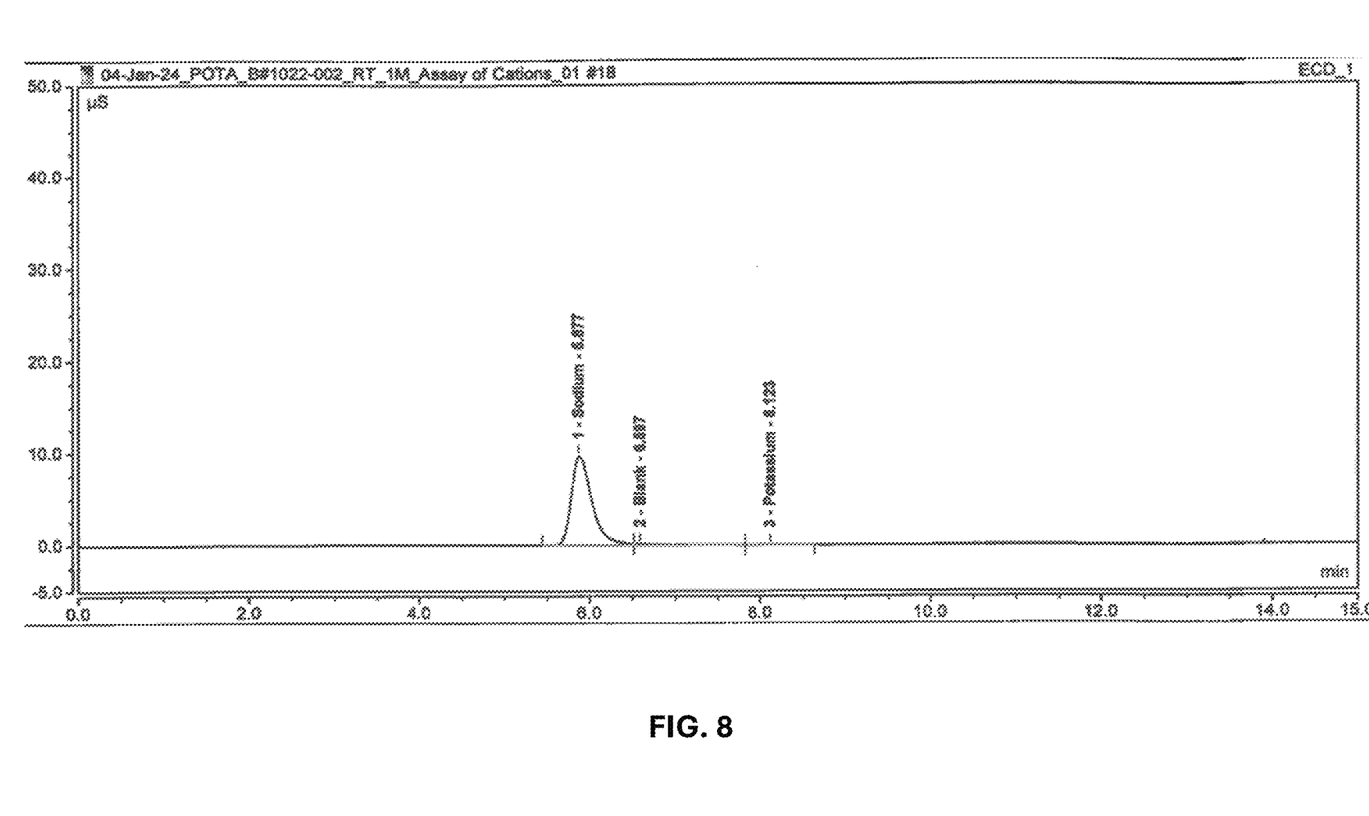
FIG. 8 is a chromatogram of a Test sample, 15 mmol P/100 mL (for Cation).
Figure 9:
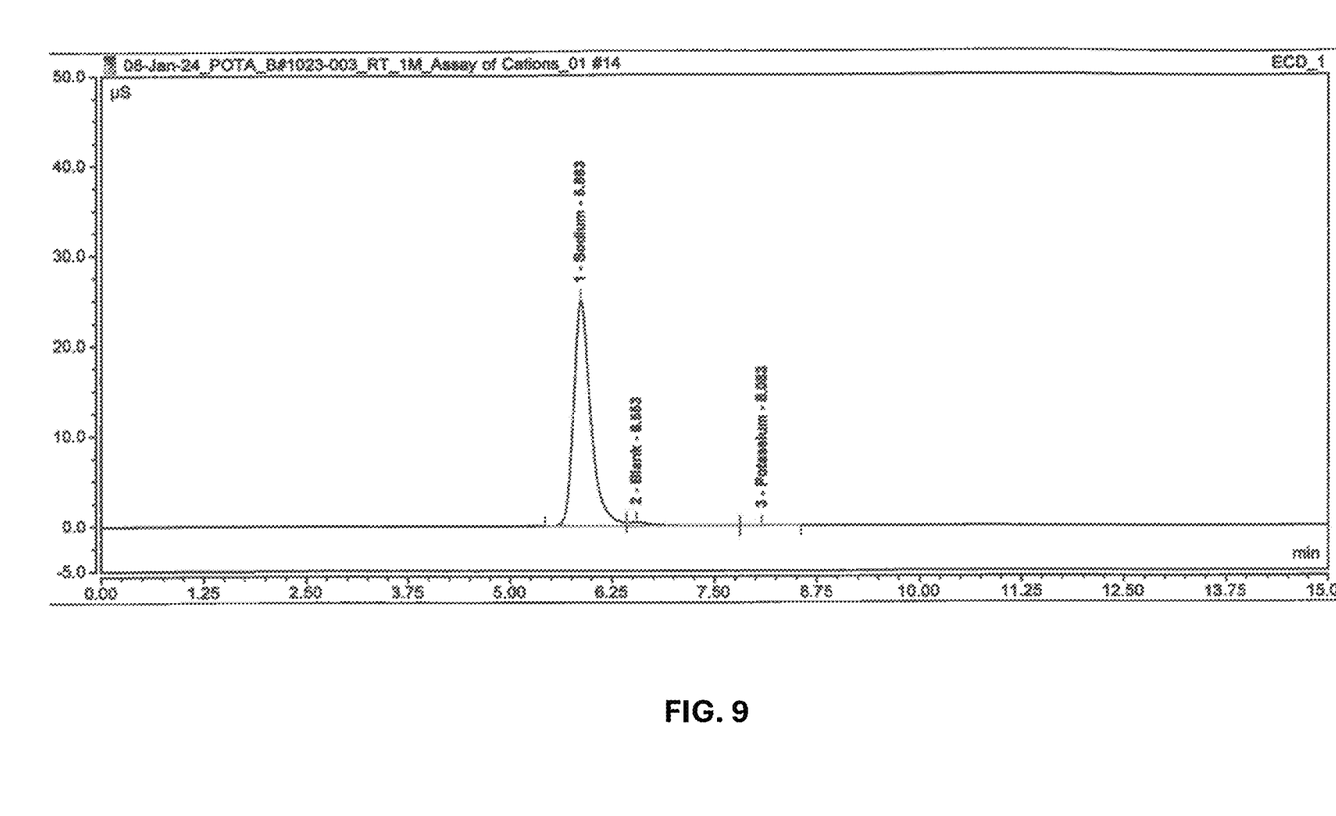
FIG. 9 is a chromatogram of a Test sample, 15 mmol P/250 mL (for Cation).

Formulation D was prepared the same as Formulation B, above, but in dextrose-containing solution. FIG. 1C shows Formulation D before terminal sterilization (at 121° C. for 15 minutes), illustrating a clear, colorless solution (CSS). FIG. 1D shows Formulation D after terminal sterilization, showing its brownish discoloration, likely due to caramelization of the sugar.

Another saline formulation, Formulation E was prepared using monobasic sodium phosphate ($NaH_2PO_4$), dibasic sodium phosphate ($Na_2HPO_4$), wherein the monobasic sodium phosphate was present in the solution an amount of about 138 mg/100 mL, the dibasic sodium phosphate was present in the solution in an amount of about 71 mg/100 mL, and sodium chloride was present at a concentration of 9.0 mg/mL. Thus, the Formulation E solution contained 1.5 mmol/100 mL phosphorus (0.015 mmol/mL) and had an aluminum content of about less than 25 mcg/L. A summary of the properties of this formulation is shown in Table 8, below.

TABLE 8

Properties of Formulation E
Sodium Phosphates Injection
(1.5 mmol of Phosphorus/100 mL) (9 mg/mL of Sodium Chloride)
Formulation E (TS @ 121° C. for 15 minutes)

| | | | Condition | | |
|---|---|---|---|---|---|
| Test | | Initial | 1M 40/15 | 3M 25/40 | 3M 40/15 |
| Description* | | CCS | CCS | CCS | CCS |
| pH of Solution | | 6.34 | 6.35 | 6.41 | 6.40 |
| Osmolality (mOsm/kg) | | 307 | 308 | 309 | 307 |
| LPC | 10 μm | 25 | 45 | 73 | 387 |
| | 25 μm | 2 | 0 | 0 | 0 |
| Assay of | % Phosphorus | 98.9% | 99.0% | 97.7% | 97.6% |
| Anions | % Chloride | 103.4% | 103.0% | 96.1% | 97.0% |
| Assay of Cations | % Sodium | 98.1% | 97.7% | 96.2% | 95.9% |
| Aluminum Content | | 3 | 3 | 4 | 2 |

*CCS-A Clear colorless solution, free from visible foreign particles

Stability was determined for all samples over various time periods and temperatures as is indicated in the respective "Stability Batches and Results, with detailed results shown in the above tables.

In further experiments, the inventors explored further formulations with phosphorus concentration ranges of between 0.015 and 0.15 mmol/mL. In that regard, it is noted that the molar ratios between the monobasic and dibasic Sodium Phosphates remained the same as those described above for formulations containing 15 mmol/100 mL phosphorus (0.15 mmol/mL). Moreover, in some embodiments contemplated phosphates solutions included sodium chloride as a tonicity agent at a concentration of about 900 mg/100 mL. However, in other embodiments the concentration of sodium chloride may also be reduced or entirely omitted. In such case, alternate tonicity agents may or may not be included and exemplary alternate agents include glycerol, mannitol, lactose, etc.

For example, in some experiments, the inventors also tested formulations having a ten-fold lower phosphorus concentration, and in particular solutions comprising Sodium Phosphates and sodium chloride in which the solution comprised 1.5 mmol/100 mL phosphorus (0.015 mmol/mL) and equal or less than 50 mcg/L aluminum. Exemplary stability data for initial formulations and stability date after terminal sterilization for 15 minutes at 121° C. In this context, it is noted that the molar ratio between the monobasic and dibasic Sodium Phosphates was the same as those described above for formulations containing 15 mmol/100 mL phosphorus (0.15 mmol/mL).

Similarly, the inventors prepared additional formulations containing 15 mmol/250 mL phosphates and depicted exemplary initial data for these formulations. Data show exemplary stability data for the formulations containing 15 mmol/250 mL. As can be seen from the data, all tested formulations were exceptionally stable even over extended periods of storage at elevated temperature.

In view of the required or recommended rates of infusion and maximum recommended concentrations, it should therefore be appreciated that the formulations presented herein will therefore be not only suitable for administration via central and peripheral lines, but can also be administered without further dilution (and potential attendant calculation errors and risk of contamination). As such, it should also be noted that the formulations presented herein can be provide in volumes suitable for a variety of patents and needs. However, it is especially preferred that the formulations presented herein will be provided in a polymeric bag at volumes of at least 50 mL and more typically at least 100 mL, and typically no more than 2,000 mL. Therefore, suitable bag volumes will contain 50 mL, 100 mL, 250 mL, 500 mL, or 1,000 mL of contemplated formulations.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sterile ready-to-use aqueous sodium phosphates solution, comprising sodium phosphates, wherein the solution comprises between 1.5 mmol/100 mL and 15 mmol/100 mL phosphorus and equal or less than 25 mcg/L aluminum, and wherein the solution has a pH of between 6.2 and 6.8.

2. The solution of claim 1, wherein the sodium phosphates comprise monobasic sodium phosphate and dibasic sodium phosphate, wherein the monobasic sodium phosphate is present in the solution an amount of between about 138 mg/100 mL and about 1380 mg/100 mL, and wherein the dibasic sodium phosphate is present in the solution in an amount of between about 71 mg/100 mL and about 710 mg/100 mL.

3. The solution of claim 1, wherein the phosphorus is present in the solution in an amount of about no more than 15 mmol/100 mL.

4. The solution of claim 1, wherein the solution is stable, after autoclaving and storage of at least 3 months at 25° C. and 40% relative humidity.

5. The solution of claim 1, wherein the solution is packaged in a flexible polyolefin container, optionally at a volume of between 100 mL and 1,000 mL, and optionally wherein the flexible polyolefin container is a flexible multilayer bag.

6. The solution of claim 5, wherein the flexible polyolefin container is further contained in a secondary metallized overwrap.

7. A sterile ready-to-use premixed pharmaceutical product stored in a flexible polymeric container, wherein the pharmaceutical product comprises sodium phosphates in an aqueous sodium chloride solution containing (a) less than 25 mcg/L aluminum, (b) between about 1.5 mmol/100 mL and 15 mmol/100 mL phosphorus, and (c) no more than about 20 mEq/100 mL sodium.

8. The pharmaceutical product of claim 7, wherein the sodium phosphates comprise monobasic sodium phosphate and dibasic sodium phosphate, wherein the monobasic sodium phosphate is present in the solution an amount of between about 138 mg/100 mL and about 1380 mg/100 mL, and wherein the dibasic sodium phosphate is present in the solution in an amount of between about 71 mg/100 mL and about 710 mg/100 mL.

9. The pharmaceutical product of claim 8, wherein the sodium chloride is present in the aqueous sodium chloride solution in an amount of between 0 mg/100 mL to about 900 mg/100 mL.

10. The pharmaceutical product of claim 7, wherein the premixed pharmaceutical product in the flexible polymeric container has a volume of between 100 mL and 1,000 mL.

11. The pharmaceutical product of claim 10, wherein the flexible polyolefin container is a flexible multilayer bag.

12. The pharmaceutical product of claim 7, wherein the flexible polymeric container is enclosed in a secondary metallized overwrap.

13. A method of administering phosphates to a patient in need of phosphorus replacement therapy, comprising:
   administering, without prior dilution, a sterile, and ready-to-use solution comprising sodium phosphates and sodium chloride solution from a flexible container to the patient at a rate of infusion and by a route of administration corresponding to the patient's age and degree of need of phosphorus replacement;
   wherein the solution comprises between 1.5 mmol/100 mL and 15 mmol/100 mL phosphorus, and less than 25 mcg/L aluminum.

14. The method of claim 13, wherein the route of administration is a central venous catheter or peripheral venous catheter.

15. The method of claim 13, wherein the solution is administered after storage of at least 3 months at 25° C. and 40% relative humidity.

* * * * *